US008394138B2

(12) United States Patent
Melsheimer et al.

(10) Patent No.: US 8,394,138 B2
(45) Date of Patent: Mar. 12, 2013

(54) MULTI-STRAND HELICAL STENT

(75) Inventors: Jeffry S. Melsheimer, Springville, IN (US); Kurt J. Tekulve, Ellettsville, IN (US); Mark R. Frye, Bloomington, IN (US); James M. Carlson, Bloomington, IN (US); Richard J. Godlewski, Bloomington, IN (US); Michael W. Hardert, Bloomington, IN (US); Jessica L. Burke, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 448 days.

(21) Appl. No.: 12/584,176

(22) Filed: Aug. 31, 2009

(65) Prior Publication Data

US 2010/0076543 A1  Mar. 25, 2010

Related U.S. Application Data

(60) Provisional application No. 61/094,627, filed on Sep. 5, 2008.

(51) Int. Cl.
*A61F 2/06* (2006.01)

(52) U.S. Cl. ...................................... 623/1.22; 623/1.51
(58) Field of Classification Search .................. 623/1.22, 623/1.51
See application file for complete search history.

(56) References Cited

U.S. PATENT DOCUMENTS

| 5,509,931 | A | * | 4/1996 | Schmitt .................. 623/1.52 |
| 6,019,779 | A | | 2/2000 | Thorud et al. |
| 6,137,060 | A | | 10/2000 | Avellanet |
| 6,159,239 | A | * | 12/2000 | Greenhalgh .............. 623/1.13 |
| 6,191,365 | B1 | | 2/2001 | Avellanet |
| 6,278,057 | B1 | | 8/2001 | Avellanet |
| 6,635,080 | B1 | | 10/2003 | Healy et al. |
| 6,685,696 | B2 | | 2/2004 | Fleischhacker et al. |
| 7,018,401 | B1 | | 3/2006 | Hyodoh et al. |
| 7,044,905 | B2 | | 5/2006 | Vidlund et al. |
| 2003/0149475 | A1 | | 8/2003 | Hyodoh et al. |
| 2004/0024443 | A1 | | 2/2004 | Dwyer et al. |
| 2004/0116960 | A1 | | 6/2004 | Demond et al. |
| 2005/0049574 | A1 | | 3/2005 | Petrick et al. |
| 2005/0075715 | A1 | | 4/2005 | Borges et al. |
| 2005/0085894 | A1 | | 4/2005 | Kershner |
| 2005/0137677 | A1 | | 6/2005 | Rush |
| 2005/0137680 | A1 | | 6/2005 | Ortiz et al. |
| 2007/0207186 | A1 | | 9/2007 | Scanlon et al. |
| 2007/0215268 | A1 | | 9/2007 | Pingleton et al. |

FOREIGN PATENT DOCUMENTS

| WO | WO 91/12779 | 9/1991 |
| WO | WO 03/057079 | 7/2003 |

OTHER PUBLICATIONS

PCT International Search Report/Written Opinion of the International Searching Authority (the European Patent Office) regarding Application No. PCT/US2009/005005 dated Nov. 16, 2009, 10 pages.

* cited by examiner

*Primary Examiner* — Thomas J Sweet
*Assistant Examiner* — Christopher D Prone
(74) *Attorney, Agent, or Firm* — Brinks, Hofer, Gilson & Lione

(57) ABSTRACT

A stent including a stent wire comprising a plurality of filaments twisted into a bundle having a helix, the stent wire bent into a pattern having a plurality of substantially straight wire sections separated by a plurality of bends. The pattern of the stent wire is spirally wound about a central axis in the same direction as the helix formed by the plurality of filaments. Each of the filaments in a bend have a cylindrical cross-section where at least one of the plurality of filaments is displaced and spaced from an immediately adjacent filament in the bend.

19 Claims, 9 Drawing Sheets

MULTI-STRAND HELICAL STENT

This application claims the benefit of priority from U.S. Provisional Application No. 61/094,627, filed Sep. 5, 2008, which is incorporated by reference.

TECHNICAL FIELD

This invention relates to endoluminal medical devices for implantation within the human or animal body for treatment of endovascular disease. In particular, this invention relates to stents and stent grafts for the treatment of endovascular disease.

BACKGROUND

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

The material used to manufacture the stent must be capable of enduring varying amounts of stress and strain once formed into a stent. Further, the stent should have the capability of going from an expanded formation into a compressed formation when the stent is placed within a delivery device. The stent must also be capable of enduring constant cycling in a corrosive atmosphere with no fatigue or weakening. One particularly useful type of stent is a z-stent. With z-stents, a given radius is required at the apex of adjoining struts of the stent that will accommodate the range of elastic deformation necessary to expand from a low profile when compressed for introduction into the deployed configuration.

Stents manufactured with a smaller radius to lower the overall profile of the stent may result in a shorter fatigue life. In addition, a stent made of a smaller diameter wire to lower the profile of the stent may have less radial force upon deployment and a shorter fatigue life. Stents having shorter strut-lengths to increase the amount of radial force may increase in the number of struts, which could lead to the stent having a higher profile.

BRIEF SUMMARY

There is a need for an improved stent having a lower delivery profile and that provides sufficient support to a diseased vessel, while having a longer fatigue life.

In one aspect, a stent is provided including a stent wire comprising a plurality of filaments twisted into a bundle having a helix, the stent wire bent into a pattern having a plurality of substantially straight wire sections separated by a plurality of bends. The stent wire is bent into a pattern having a plurality of substantially straight wire sections separated by a plurality of bends. The pattern of the stent wire is spirally wound about a central axis in the same direction as the helix formed by the plurality of filaments. The each of the filaments in a bend have a cylindrical cross-section where at least one of the plurality of filaments is displaced and spaced from an immediately adjacent filament in the bend.

In another aspect, a stent is provided a stent wire comprising a plurality of filaments twisted into a bundle having a helix, the stent wire bent into a pattern having a plurality of substantially straight wire sections separated by a plurality of bends. Each of the filaments in a bend have a cylindrical cross-section and where at least one of the plurality of filaments is displaced and spaced from an immediately adjacent strand in the bend In yet another aspect, a prosthesis is provided having a graft composed of biocompatible material formed into a tubular configuration having lumen disposed therethrough. A stent is disposed about a surface of the graft comprising a plurality of filaments twisted into a bundle having a helix, each filament having a cylindrical cross-section, the plurality of filaments bent into a pattern having a plurality of substantially straight wire sections separating a plurality of bends. At least one of the plurality of filaments in a bend is displaced and uniformly spaced from an immediately adjacent strand in the bend.

In one example, the bundle of filaments is bent into a pattern having a plurality of substantially straight sections separating a plurality of bends, where each of the filaments is displaced and uniformly spaced from an immediately adjacent filament about each bend.

BRIEF DESCRIPTION OF THE DRAWINGS

The prosthesis may be better understood with reference to the following drawings and description. The components in the figures are not necessarily to scale, emphasis instead being placed upon illustrating the principle of the disclosure. Moreover in the figures, like referenced numerals designate corresponding parts throughout the different views.

DETAILED DESCRIPTION OF THE DRAWINGS AND THE PRESENTLY PREFERRED EMBODIMENTS

Figure 1:
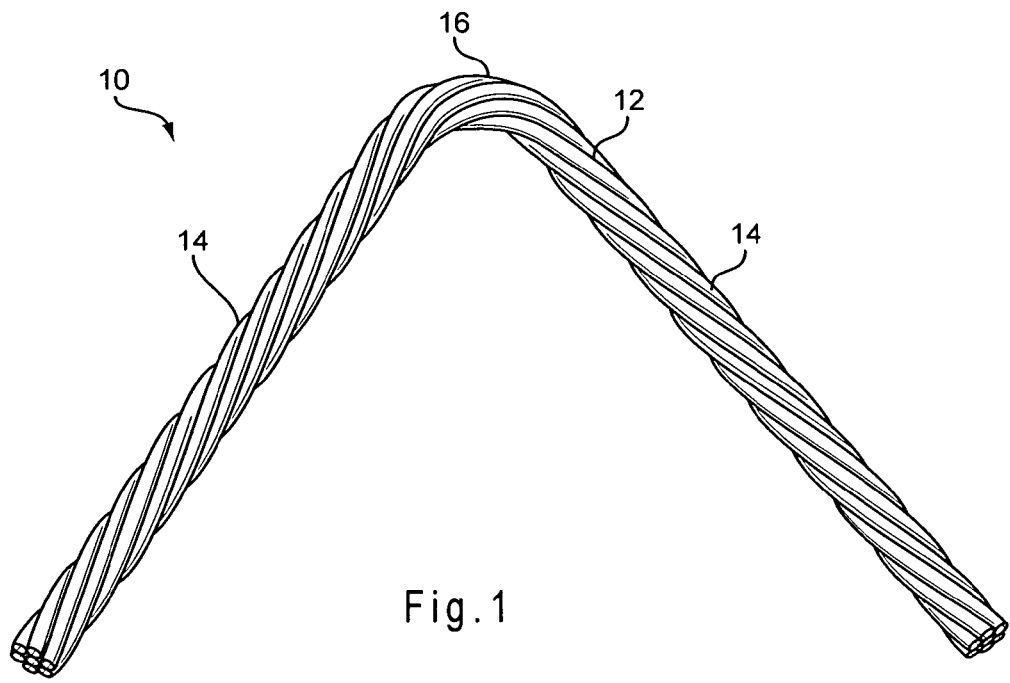
FIG. 1 shows a stent wire formed by twisting a plurality of filaments into a bundle.

Unless defined otherwise, all technical and scientific terms used herein have the same meaning as commonly understood to one of ordinary skill in the art to which this invention belongs.

The terms "distal" and "distally" are intended to refer to a location or direction that is, or a portion of a device that when implanted is further downstream in the direction of or with respect to blood flow. The terms "proximal" and "proximally" are intended to refer to a location or direction that is, or a portion of a device that when implanted is further upstream in the direction of or with respect to blood flow.

The term "prosthesis" means any replacement for a body part or function of that body part. It can also mean a device that enhances or adds functionality to a physiological system.

The term "tubular" refers to the general shape of an endoluminal device which allows the module to carry fluid along a distance or fit within a tubular structure such as an artery. Tubular prosthetic devices include single and both branched and bifurcated devices.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a member selected from the group comprising: blood vessels, respiratory ducts, gastrointestinal ducts, and the like. "Endoluminal device" or "endoluminal prosthesis" thus describes devices that can be placed inside one of these lumens.

The term "stent" means any device or structure that adds rigidity, expansion force or support. A stent is used to obtain and maintain the patency of the body passageway while maintaining the integrity of the passageway. The stent may be located on the exterior of the device, the interior of the device, or both. A stent may be self-expanding, balloon-expandable or may have characteristics of both. A variety of other stent configurations are also contemplated by the use of the term "stent."

The term "graft" or "graft material" describes an object, device, membrane, or structure that is joined to or that is capable of being joined to a body part to enhance, repair, or replace a portion or a function of that body part. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto a mandrel. Preferably, polymers, although added in layers onto the mandrel, after curing, result in one layer that encapsulates a stent or woven graft. This also aids in decreasing the incidence of delamination of the resulting endovascular prosthesis. A stent may be attached to a graft to form a "stent graft."

The term "yarn" refers to a length of a continuous thread or strand of one or more filaments or fibers, with or without twist, suitable for weaving, knitting or otherwise intertwining to form a textile fabric.

The terms "patient," "subject," and "recipient" as used in this application refer to any mammal, especially humans.

A stent is formed from a stent wire having a plurality of filaments twisted in a coil formation. The coiled stent wire may be bent into a pattern having a plurality of substantially straight wire sections separated by a plurality of bends. The pattern also may be spirally wound about a central axis, where it defines a tubular shape. Preferably each of the filaments has a cylindrical cross-section at least in the area of the bends of the pattern. Also, preferably, the filaments are displaced and spaced from an immediately adjacent filament about each bend.

FIG. 1 shows a stent wire 10 formed by twisting a plurality of individual filaments 12 to form a coiled wire. As shown, each of the filaments 12 has a substantially cylindrical cross-section. The stent wire 10 preferably includes at least three individual filaments 12. As shown in FIG. 1, the stent wire 10 includes seven individual filaments 12. The stent wire 10 preferably is not drawn through a die. The filaments 12 of the stent wire 10 may be twisted either in the "right hand" direction or the "left hand" direction.

A stent may be formed of stent wire 10 forming the stranded stent wire 10 into a spiral having a repeating pattern of alternating straight sections 14, or struts, and bends 16. For example, the stent wire 10 may be formed into a helix or spiral of a repeating zig zag pattern such as those shown in FIGS. 10a-10d. In other embodiments, the stent wire 10 may be formed into other configurations, including a single crown stent or multiple crown stents.

When the stent wire 10 is formed into a pattern of alternating straight sections 14, or struts, and bends 16, the plurality of individual filaments 12 preferably have a uniform twist throughout struts 14, such that the individual filaments 12 remain in close proximity. The individual filaments 12 are of a biocompatible material. The materials used in the manufacture of the device may be selected from a well-known list of suitable metals. Preferred materials include those materials that can provide the desired functional characteristics with respect to mechanical load bearing, biological compatibility, modulus of elasticity, or other desired properties. In various embodiments, the stent wire 10 may include a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy.

Figure 2:
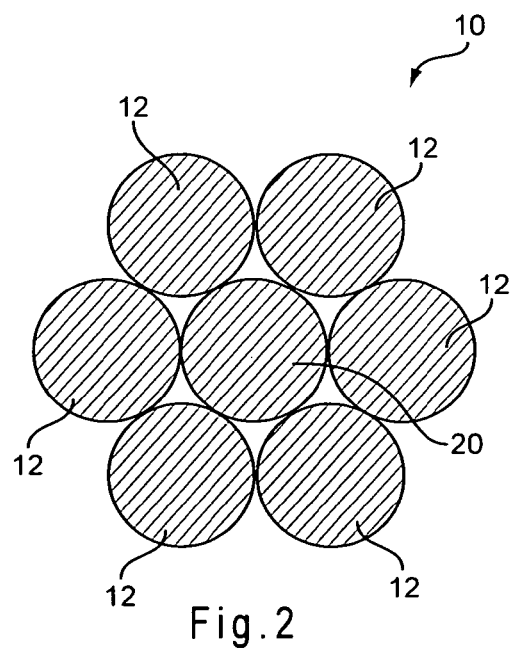
FIG. 2 shows a cross-section of the wire shown in FIG. 1.

FIG. 2 shows cross section of the stent wire 10 of FIG. 1. As shown, a central mandrel filament 20 is surrounded by six perimeter filaments 12. The central mandrel filament 20 may be manufactured from the same material used for the perimeter filaments 12, or from other materials. In some embodiments, the central mandrel filament 20 may be manufactured from a different material than the perimeter filaments 12, such a radiopaque material. In other embodiments, one of the perimeter filaments may comprise a radiopaque material. Although FIG. 2 shows a stent wire 10 having seven filaments twisted into a coil, other numbers of filaments also may be used.

Figure 3:
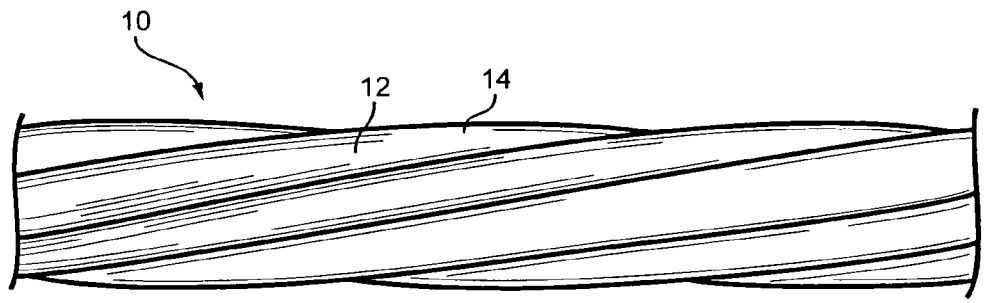
FIG. 3 shows a partial side view of a straight section of the stent wire shown in FIG. 1.

FIG. 3 shows a partial side view of a straight section of the stent wire 10 shown in FIG. 1. As shown in FIG. 3, the seven filaments 12 forming the stent wire 10 have minimal contact with the central mandrel filament 20 throughout the stent 10. In this embodiment, the central mandrel filament 20 is configured such that it is equidistant from the perimeter filaments 12.

Figure 4:
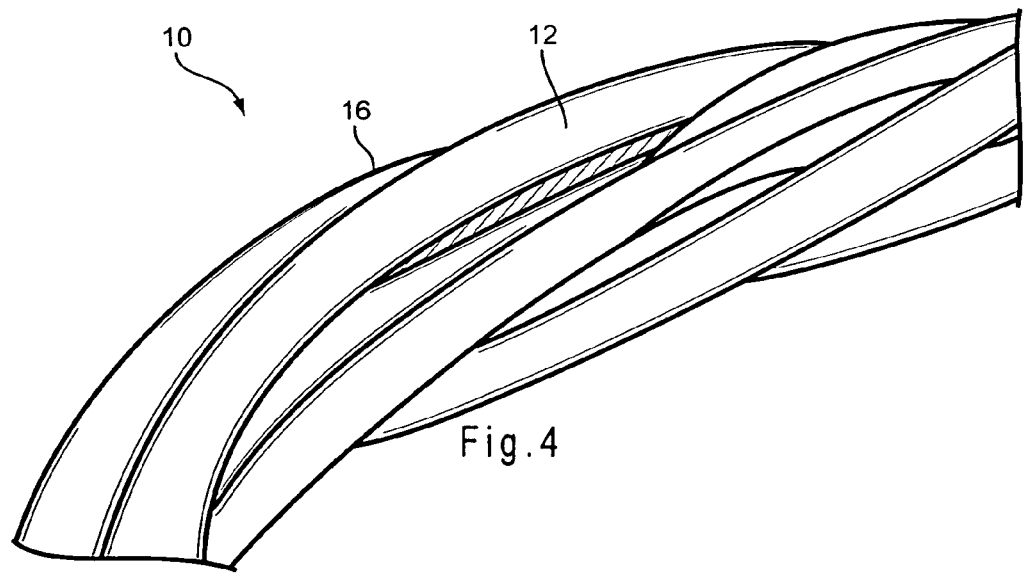
FIG. 4 shows a partial side view of a bend of the stent wire shown in FIG. 1.

FIG. 4 shows a partial side view of a bend 16 of a stent wire 10. As shown, the individual filaments 12 have a substantially cylindrical profile at least within the area of the bend 16. The cylindrical profile of the individual filaments 12 allows for the smallest possible surface area for a given cross-sectional area. In a preferred embodiment, at least one of the individual filaments 12 is displaced from the remaining strands in the area of the bend 16. An equal distribution of stress along the surface of the individual filaments 12 is experienced as they are being formed into a bend 16. The amount of stress present throughout the bend 16 is greater upon the individual perimeter strands 12 of the stent 10 than the central mandrel strand 20. The cylindrical profile of individual filaments 12, when formed into a stent, help prevent shearing upon the walls of the vessel of the patient. Furthermore, the cylindrical profile of the individual filaments 12 help prevent the effects of shearing upon another endovascular device, such as a graft, which will be discussed below. In this embodiment, the individual perimeter filaments 12 have minimal contact with the central mandrel strand 20.

Figure 5:
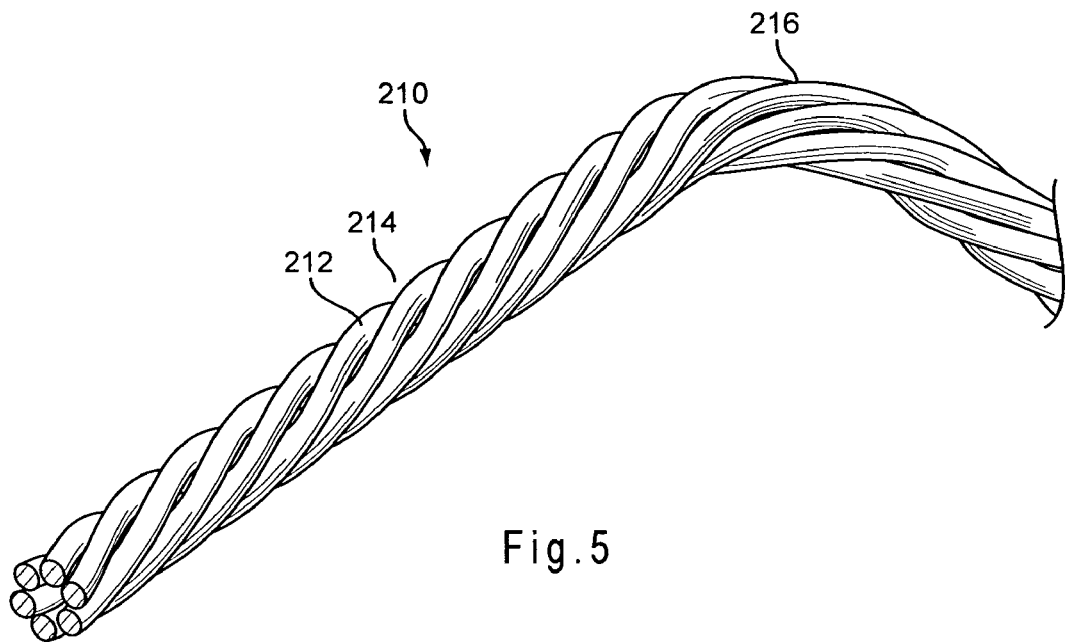
FIG. 5 shows a partial perspective view of a stranded stent wire without a central mandrel strand.
Figure 6:
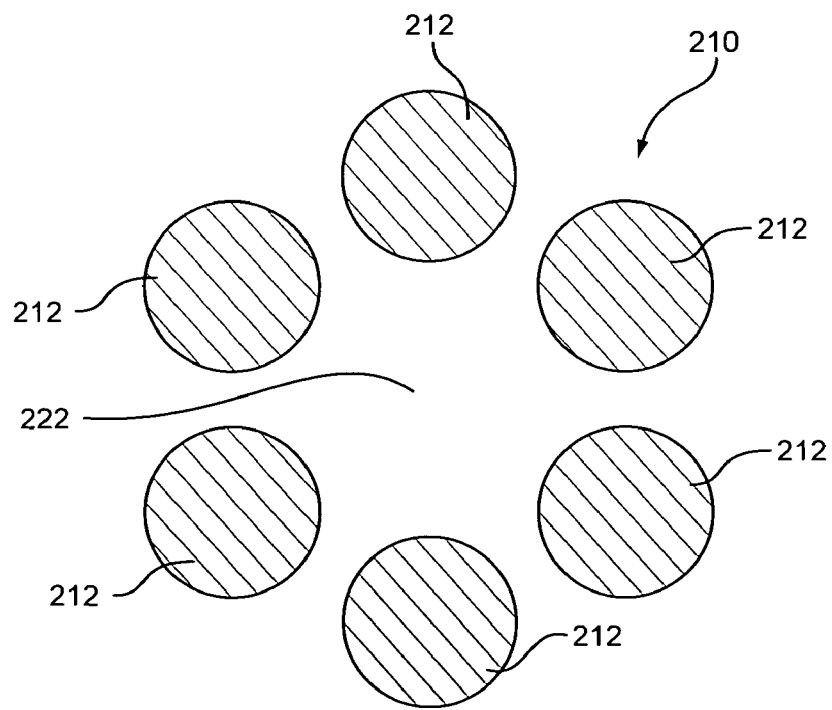
FIG. 6 shows a cross-sectional view of the stent of FIG. 5.

An alternative embodiment of a stent wire 210 is shown in FIGS. 5 and 6, which the stent wire 210 is formed without a central mandrel core wire. The stent 210 includes six individual perimeter filaments 212. An opening 222 is disposed through the center of the perimeter filaments 212. Throughout the area of the bend 216, there is very little or no contact between any of the individual filaments 212. Throughout the bend, adjacent filaments have very little or no contact with one another regardless of the number of filaments, or the presence or absence of a central filament.

Figure 7:
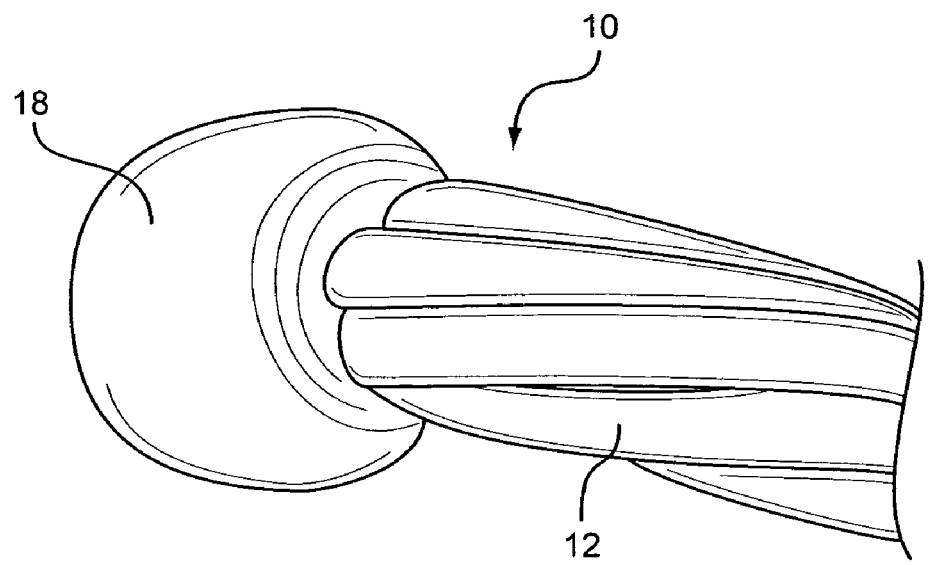
FIG. 7 shows an embodiment of a stent where the ends of the filaments are joined together by a welded/soldered ball.
Figure 8:
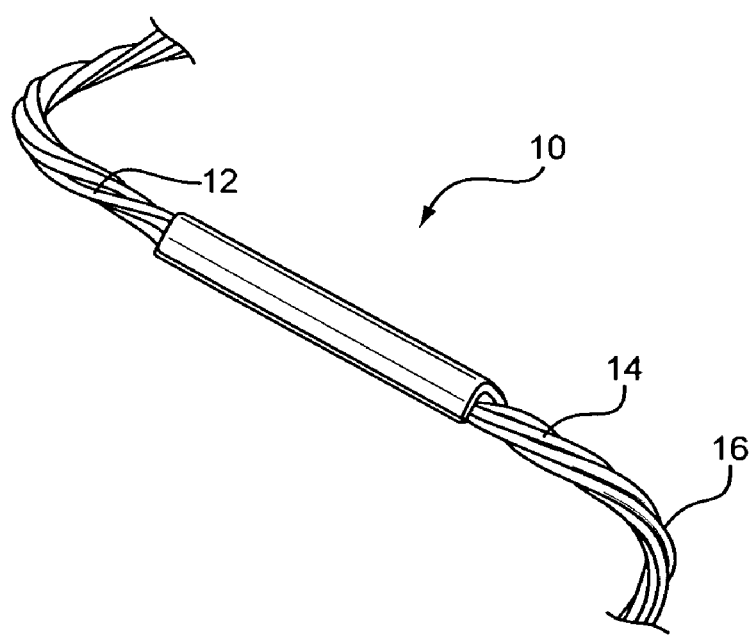
FIG. 8 shows an embodiment a stent where the ends of the filaments are joined together by a piece of cannula.

As shown in FIGS. 7 and 8, the ends 18 of the stent wire 10 may be joined together by a variety of different methods. In one embodiment, the ends of the individual filaments 12 may be formed into a ball 18, as shown by FIG. 7. The ball 18 may be formed by suitable techniques known to one of ordinary skill in the art, including laser welding or TIG welding. FIG. 8 shows another embodiment where the ends of the individual filaments 12 are joined together by a piece of cannula soldered about its length.

In forming a stent made from stent wire 10, the individual filaments 12 are formed into a bundle having a diameter of between about 0.250 mm to about 0.500 mm, and preferably between about 0.320 mm and about 0.410 mm and more preferably between about 0.345 mm and about 0.355 mm. In one example the diameter of the stent wire 10 is about 0.4064 mm.

Figure 9:
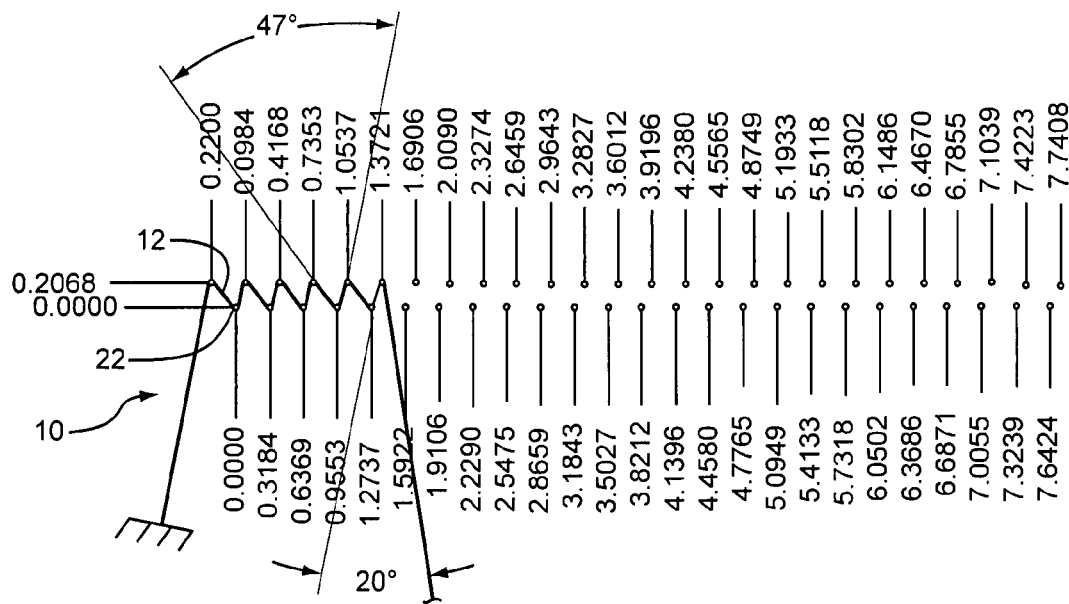
FIG. 9 shows the formation of an embodiment of a stent.

As shown in FIG. 9, to form a stent from stranded wire 10, stranded wire 10 is bent about a series of pins 22 having an average diameter of about 0.96 mm. The stranded wire 10 is over-bent around each pin 22 to an included angle of about $20°±10°$ in order to compensate for the effects of spring-back by the individual filaments 12. The resulting stent 10 has an inner radius of about 0.51 mm. In one embodiment, the resulting stent 10 consists of five apices per revolution and the struts 14 of the stent 10 average a length of about 8 mm. In forming a stent, such as that shown in FIG. 1, the stranded wire 10 is bent around the series of pins such that they have an angular formation measuring from about 30° to about 60°, preferably from about 37° to about 55°, and more preferably from about 45° to about 49°. In one example, the struts 14 of the stent wire 10 are bent around the series of pins such that they have an angular formation measuring about 47°.

In one embodiment, the individual filaments 12 are held under 1.8 kg/m·s$^2$ of tension and not allowed to spin as they are twisted in a left-hand formation. When the bending process is complete, the resulting stent is removed from the pins. In this unconstrained state, the plurality of bends of the formed stent have an angular formation measuring from about 75° to about 90°, preferably from about 80° to about 85°. In one example, each bend forms an angle of about 83°.

Referring now to FIGS. 10a-10d, the stent wire 10 may be formed into various helical or spiral configurations. Preferably, the stent wire 10 is spirally wound about a central axis to define a tubular shape. The stent is spirally wound in the same direction the filaments 12 are twisted. FIGS. 10a-10d show separate stent sections comprising multiple filament stranded wires 10 that may be used to form a stent.

Figure 10B:
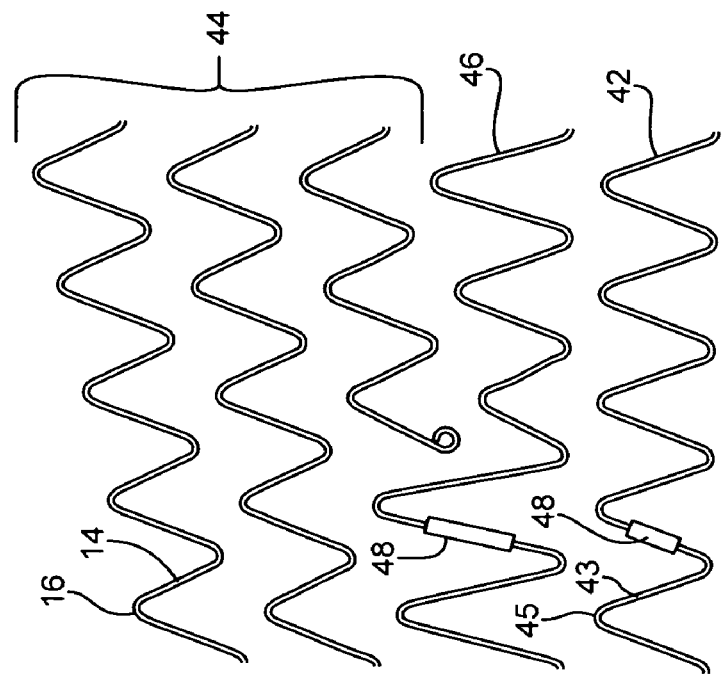
FIGS. 10a-10d show various embodiments of a stent in a spiral configuration, and in a single-loop configuration.
Figure 10A:
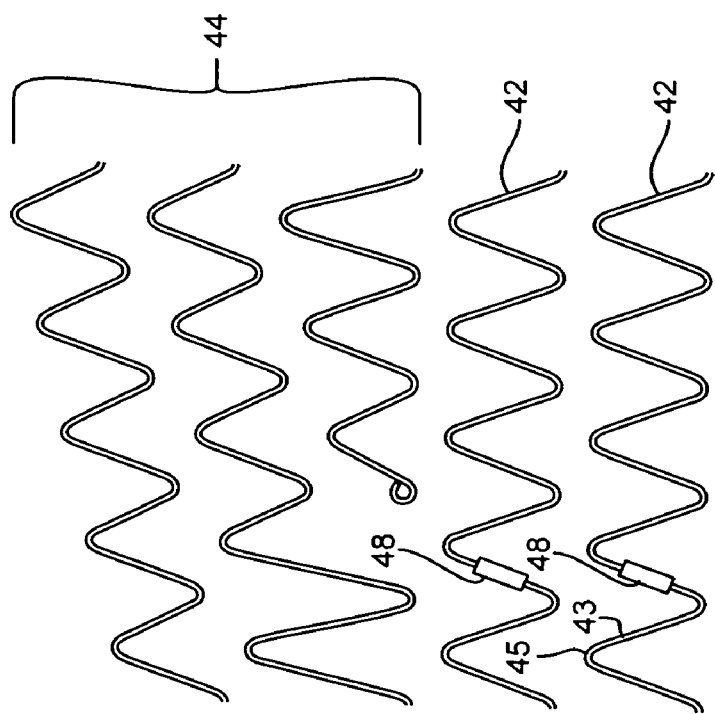
Figure 10D:
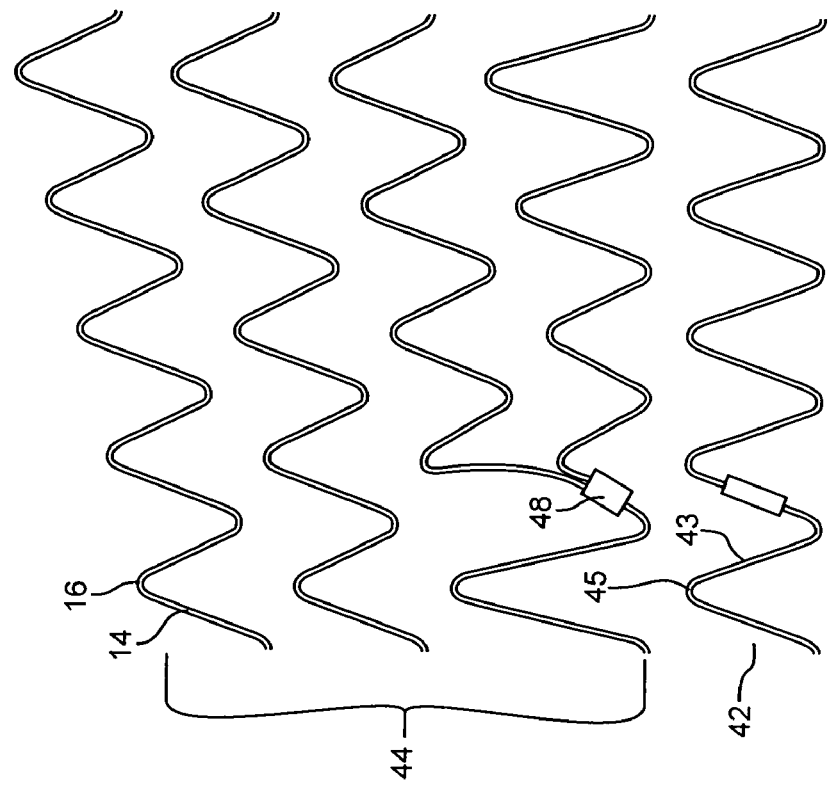
Figure 10C:
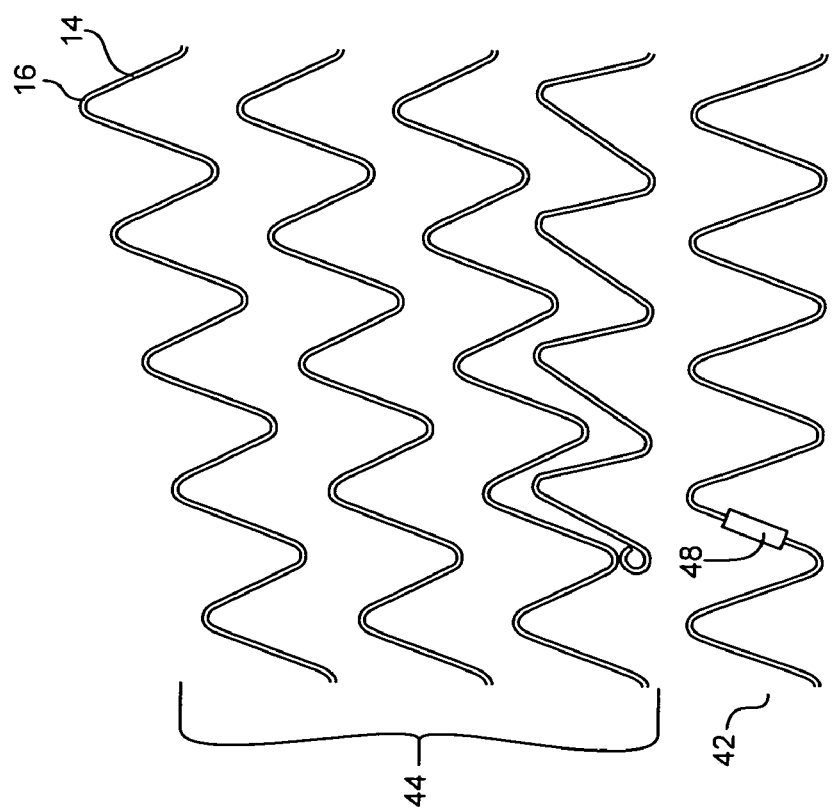

As shown in FIGS. 10a, 10b, and 10d, stent section 42 includes a plurality of straight sections 43 and a plurality of bends 45, where the ends are joined together by a cannula 48. Stent section 42 may be affixed within the ends of a graft (not shown) in order to anchor the device within the vessel, and/or exert sealing force between overlapping sections of individual grafts. Stent section 44 depicts a plurality of individual filaments, where the struts are all the same different length. Stent section 44 discloses a spiral formation that may be affixed about the outer surface of a graft 30. FIGS. 10a-10d depict a stent section 44 having a plurality of individual filaments, as shown in FIG. 1, where the struts are all the same length. FIG. 10b also includes a segment 46 configured to accommodate the transition from spiral-stent with unequal-length legs, to loop-stents with equal-length legs. FIGS. 10a, 10b, and 10c show embodiments where a portion of the stent segment 44 is joined to a portion of the stent segment 42 itself. FIG. 10d shows an embodiment where the stent section 44 is joined to itself by a piece of cannula.

Figure 11:
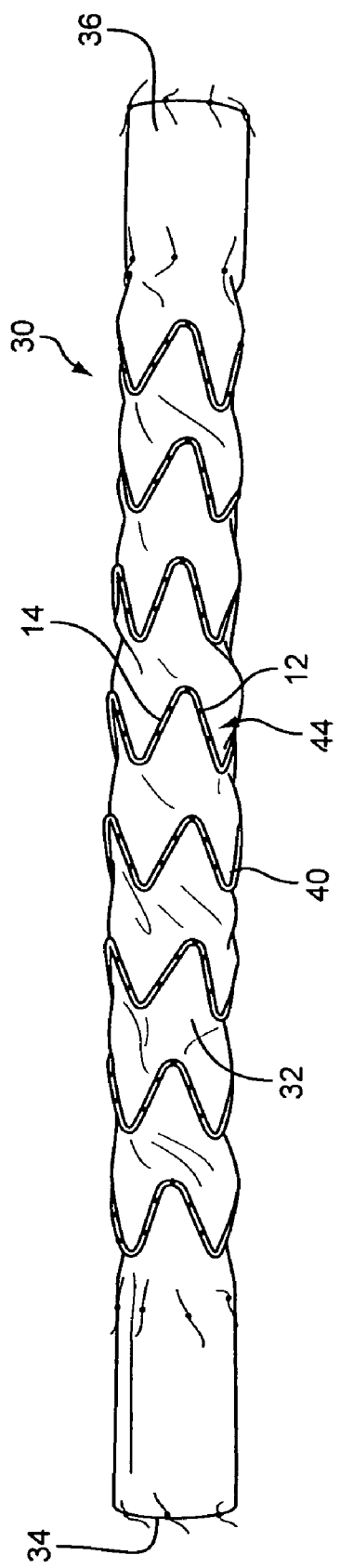
FIG. 11 shows a stent-graft including a spirally wound wire formed from a stranded stent wire.
Figure 12:
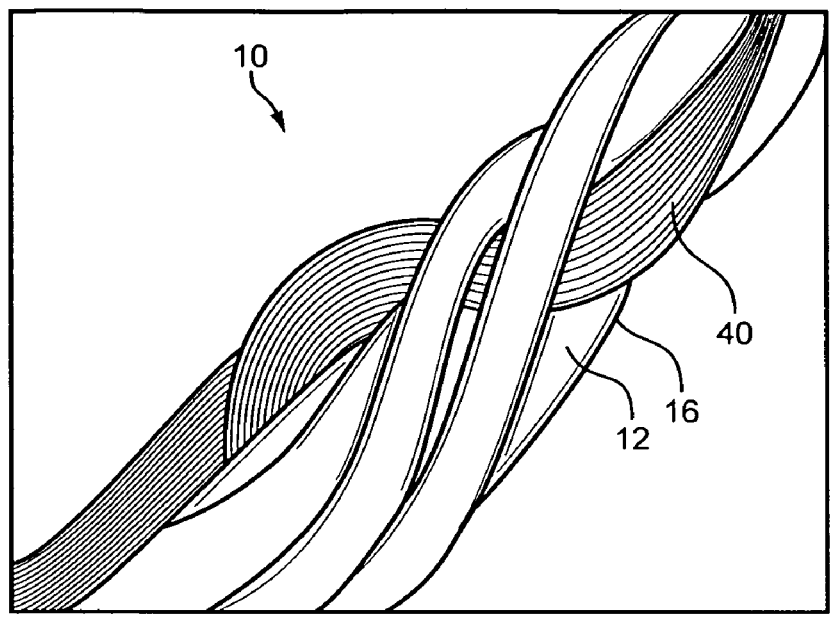
FIG. 12 shows a partial view of a stranded stent wire where a suture is placed between displaced filaments.

Referring now to FIG. 11, a stent 11 formed from stent wire 10 may be affixed to another endovascular material, such as a graft 30. As shown in FIG. 8, the graft 30 has a tubular configuration forming a wall 32 having a first end 34 and a second end 36. The wall 32 of the tubular graft 30 defines a central lumen that generally is smooth in order to not inhibit the passage of the intended fluid. The stent 11 may be secured to the graft 30 by suture material 40. When the stent 11 is attached to the graft 30, the amount of displacement between at least one of the individual filaments 12 may depend upon by the tautness of the attaching sutures 40. In this embodiment, the suture material 40 is secured to the graft material about the bundle of strands. In other embodiments, as shown in FIG. 12, the suture material 40 may be placed within the displaced filaments at each bend 16, which helps to distribute the spacing between each filament strand 12. Furthermore, placing that attachment sutures between the individual filaments 12 prohibits movement between the graft material 30 and the stent 11. Alternatively embodiments, the suture material 40 may be placed between the individual filaments in the straight sections of the stent 11.

The stent 11, which has individual filaments 12 twisted in a left-hand direction, is sewn onto the graft 30 in a left-handed spiral, creating a plurality of stent rows. Since the stent 11 is sewn onto the graft 30 in the spiral formation, there will be a plurality of stent rows present. The rows are designed such that they have a uniform amount of space between each row measuring from about 1 mm to about 7 mm, preferably from about 3 mm to about 5 mm. In one example, each row is spaced about 4 mm apart from any other adjacent row. The stent 11 is sewn onto the graft such that the struts of the stent have an angular formation measuring about measuring from about 45° to about 60°, preferably from about 50° to about 55°. In one example, the stent 11 is sewn onto the graft such that the bends of the stent have an angular formation measuring about 53°.

When the stent 11 is attached to the graft 30 to form a stent-graft, advantages are found when the stent-graft is caused to take on a given curvature. Generally, when a stent-graft is forced into a curved shape, the graft material is put in tension on the outside of the curve, and may buckle on the inside of the curve and form large folds. However, stent grafts incorporating a stent as described here will tend to distribute stress amongst the plurality of rows created by the spiral formation, which promotes a tendency for a greater multitude of smaller folds. This feature allows the stent-graft to be more flexible when placed in damaged areas in curved vessels. In addition, due to the individual filaments working together to provide the radial force, the straight sections may be of a shorter length than those of a stent constructed of only a larger, single wire.

Figure 13:
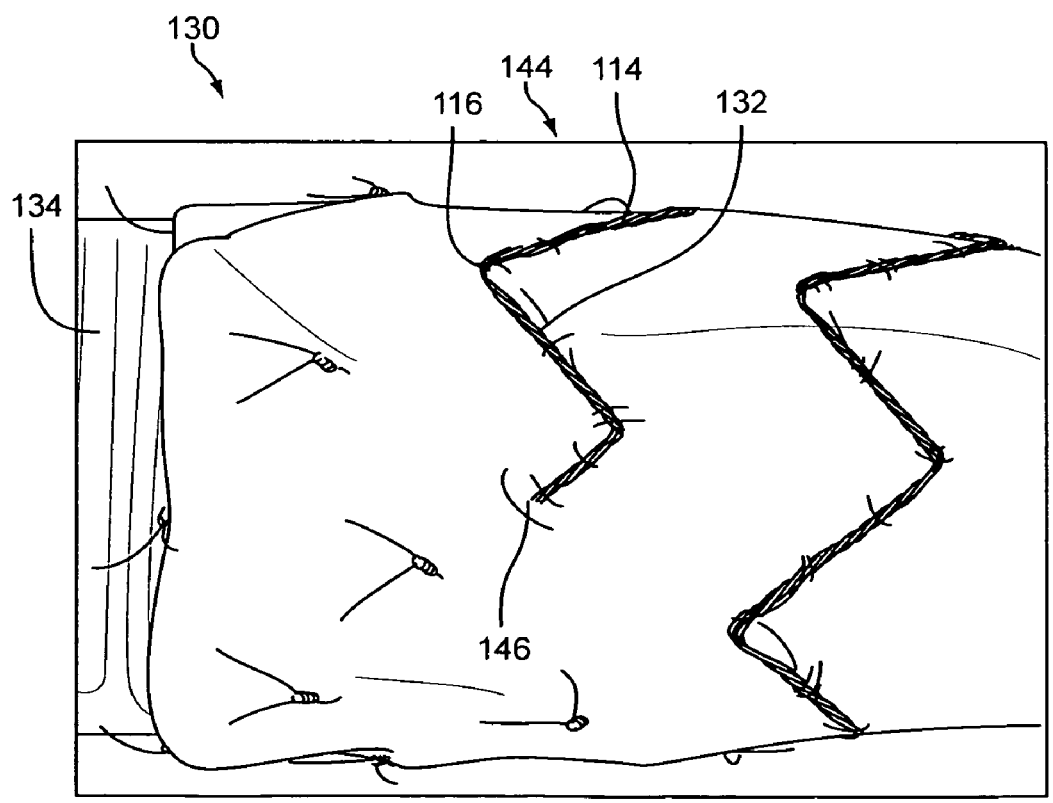
FIG. 13 shows another embodiment of a stent-graft having a stent formed from a stranded stent wire.

FIG. 13 another stent graft 130 having a stent formed from a coiled stent wire. In this embodiment, the stent segment 144 extends to both a first end 134 and a second end of the graft 130. Generally, a first end 134 of the graft 130 may be required to seal against the interior wall of a vessel and maintain an anchorage within the vessel. A second end 136 of the graft 130 may also be required to provide a seal against the interior of a previous placed stent graft or at a distal end of the vessel. As shown by FIG. 13, the spiral pattern of the stent segment 144 may begin within the interior surface 135 of the graft at the first end 134. The stent segment 144 continues along the interior surface of the graft 130 for a pre-determined distance. The tubular graft 130 is preferably comprised of woven material, where the weave is tight enough to carry fluid while still maintaining flexibility. A small perforation 146 is placed within the wall 132 of the graft 130 by a device, such as an awl, which parts the individual yarns of the wall of the tubular graft 130. This perforation 146 provides a passageway which may seal snugly around the impenetrating stent segment 144. The stent segment 144 is then continued along the outer surface of the tubular graft 130 until it approaches the second end. A second perforation is placed within the wall and the stent segment 144 is passed through the second perforation and taken inside of the tubular graft 130. The spiral stent pattern is continued without interruption until termination at the second end.

The tubular graft material used to form a stent graft described here is preferably constructed from a biocompatible material. The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile graft, provided the final textile is biocompatible. Textile materials that can be formed into fibers suitable for making textile grafts include polyethylene, polypropylene, polyaramids, polyacrylonitrile, nylons and cellulose, in addition to polyesters, fluorinated polymers, and polyurethanes as listed above. Preferably the textile is made of one or more polymers that do not require treatment or modification to be biocompatible. The graft is preferably constructed from a material such as woven multifilament polyester. One example of biocompatible polyester include Dacron™ (DuPONT, Wilmington, Del.), which is known to be sufficiently biologically inert, non-biodegradable, and durable to permit safe insertion inside the human body. Polyester is also known to excite fibrous ingrowth which will secure the graft 30 to the wall of the lumen within a few months of its insertion. Any material with such qualities may be used, however.

It is therefore intended that the foregoing detailed description be regarded as illustrative rather than limiting, and that it be understood that it is the following claims, including all equivalents, that are intended to define the spirit and scope of this invention.

The invention claimed is:

1. A stent, comprising
a stent wire comprising a plurality of filaments twisted into a bundle having a helix, the stent wire bent into a pattern having a plurality of substantially straight wire sections separated by a plurality of bends;
the pattern being spirally wound about a central axis in the same direction as the helix formed by the plurality of filaments; and
where each of the filaments in a bend has a cylindrical cross-section and where at least one of the plurality of filaments is displaced and spaced from an immediately adjacent filament in the bend.

2. The stent of claim 1, where the stent comprises at least three filaments.

3. The stent of claim 1, where the plurality of filaments further includes a central core wire.

4. The stent of claim 1, where the plurality of filaments have no contact with adjacent filaments throughout the length of the plurality of bends.

5. The stent of claim 1, where each of the filaments have a uniform cylindrical cross-section throughout the length of each filament.

6. A stent, comprising:
a stent wire comprising a plurality of filaments twisted into a bundle having a helix, the stent wire bent into a pattern having a plurality of substantially straight wire sections separated by a plurality of bends;
where each of the filaments in a bend have a cylindrical cross-section and where at least one of the plurality of filaments is displaced and spaced from an immediately adjacent strand in the bend.

7. The stent of claim 6, where the stent comprises at least three filaments.

8. The stent of claim 7, where the plurality of filaments further includes a central core wire.

9. The stent of claim 6, where the plurality of bends have an angular formation measuring from about 75° to about 90°.

10. The stent of claim 9, where the plurality of bends of the formed stent have an angular formation measuring about 83°.

11. The stent of claim 10, where the pattern is wound in the same direction as the helix formed by the plurality of filaments.

12. The stent of claim 6, where each of the plurality of filaments have a uniform cylindrical cross-section throughout the length of each filament.

13. The stent of claim 6, where the pattern is spirally wound about a central axis.

14. The stent of claim 6, where the plurality of filaments have no contact with adjacent filaments throughout the length of the plurality of bends.

15. A prosthesis, comprising:
a graft composed of biocompatible material formed into a tubular configuration having lumen disposed therethrough; and
a stent disposed about a surface of the graft comprising a plurality of filaments twisted into a bundle having a helix, each filament having a cylindrical cross-section, the plurality of filaments bent into a pattern having a plurality of substantially straight wire sections separating a plurality of bends;

where at least one of the plurality of filaments in a bend is displaced and uniformly spaced from an immediately adjacent strand in the bend.

16. The prosthesis of claim 15, where the stent includes seven individual filaments.

17. The prosthesis of claim 15, where the stent and the individual filaments are spirally wound such that the stent and the individual filaments have the same chirality.

18. The stent of claim 15, where the plurality of filaments are evenly spaced and displaced apart from each adjacent stand.

19. The stent of claim 15, where a portion of the stent is spirally wound within an inner surface of a proximal end and an inner surface of a distal end of the graft.

* * * * *